United States Patent

Johnson et al.

[11] 4,033,774
[45] July 5, 1977

[54] DENTAL IMPRESSION COMPOUND

[76] Inventors: Paul A. Johnson, 14040 N. Birchwood Lane, Mequon, Wis. 53092; Hamilton A. Pinkalla, 7656 W. Forest Home Ave., Milwaukee, Wis. 53220

[22] Filed: Apr. 8, 1976

[21] Appl. No.: 675,047

[52] U.S. Cl. .................................. 106/35; 106/241
[51] Int. Cl.² .................... C08L 93/04; C09K 3/00
[58] Field of Search .............. 106/35, 38.5 D, 38.6, 106/239–241

[56] References Cited
UNITED STATES PATENTS 2,077,418  4/1937  Kelly .............................. 106/241
2,248,999  7/1941  Johnson .......................... 106/35

*Primary Examiner*—Theodore Morris
*Attorney, Agent, or Firm*—Henry C. Fuller

[57] ABSTRACT

A dental impression composition is formulated from a hydrogenated wood rosin, petrolatum, aluminum powder and talc and includes the following characteristics: (1) good plastic flow at mouth temperature to provide adequate working time with low flow at room temperature; (2) good heat and light stability which affords good shelf life with no change in flow properties; (3) flow properties not changed during extensive heating and sterilization during preparation for application on the dental tray; (4) sufficient, but not excessive adhesion strength so that the composition adheres to the tray but not to the patient's wet tissues; and (5) low thermal-expansion coefficient so that there are no dimensional changes as the impression is cooled from mouth temperature and (6) good definition of detail.

4 Claims, 2 Drawing Figures

DENTAL IMPRESSION COMPOUND

BACKGROUND OF INVENTION

A dental impression compound suitable for soft, mobile tissue should meet the following requirements:

1. have good plastic flow at mouth temperature with a minimum of 85% at 37° C.
2. set quickly when exposed to temperatures slightly below that of the mouth;
3. should unite into a solid mass without adhering to mouth tissues or plaster cast material but should adhere to the tray material;
4. give a good negative reproduction of the dimensions and surface detail of the mouth tissues without displacing the detail from its true position;
5. good dimensional stability at temperatures below that of the mouth so that it will not deform in any way because of temperature changes, atmospheric conditions, or the pouring of a plaster cast;
6. should not be unpleasant or toxic to the patient;
7. should have good shelf life;
8. should be easy and convenient to use; and
9. capable of sterilization when in the container in which it is supplied.

Of the commercially available impression compounds known to applicant, EX-3-N-Gold apparently made in accordance with the disclosure in German patent 1,067,175, has the most desirable plastic flow at mouth temperature. However, an impression compound made in accordance with German patent 1,067,175 cannot be sterilized in an autoclave without affecting its properties.

SUMMARY OF INVENTION

The dental impression composition disclosed herein achieves the foregoing objectives. The impression compound has a flow rate of 85% as hereinafter defined at mouth temperature, and a substantially lesser flow rate at room temperature and thus, sets quickly when removed from the mouth. The impression compound gives good reproduction of detail and is easy to work with. The substances employed in the composition, namely, hydrogenated wood rosin, white petrolatum and with a filler comprising talc and aluminum powder provide a heat and light stable composition which can be sterilized prior to use without changing its properties.

Further objects, features and advantages of the invention will become apparent from the following disclosure.

DESCRIPTION OF PREFERRED EMBODIMENT

Figure 1:
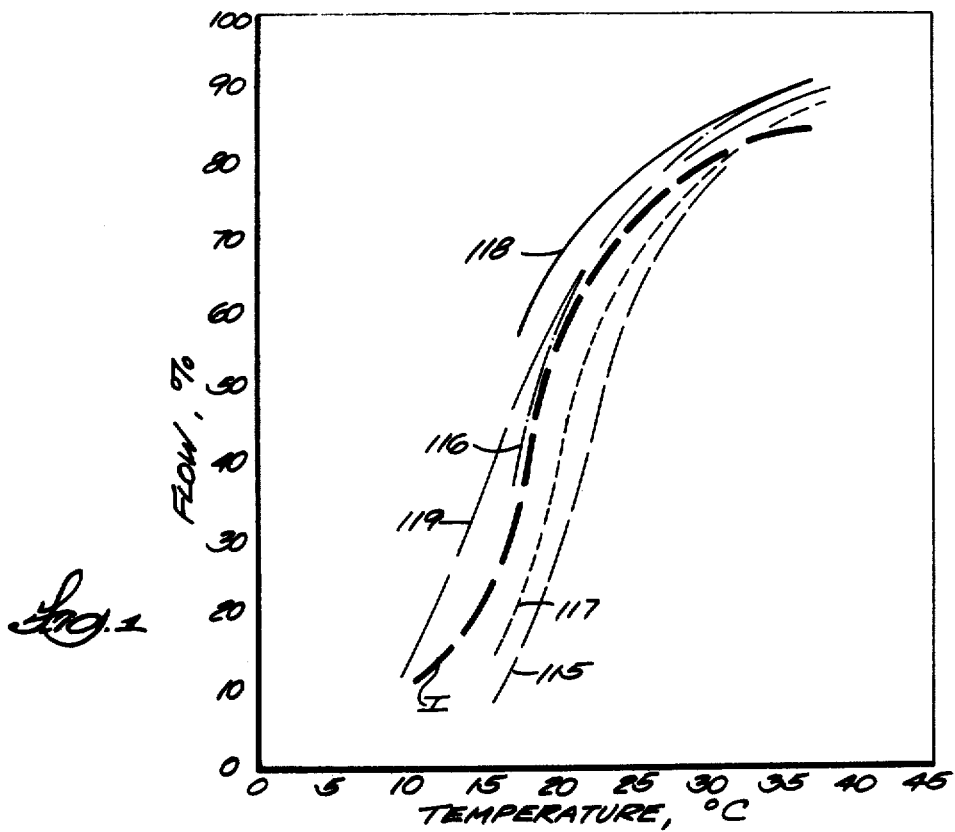
FIG. 1 is a group of curves showing the percent of flow versus temperature for five compositions tested.
Figure 2:
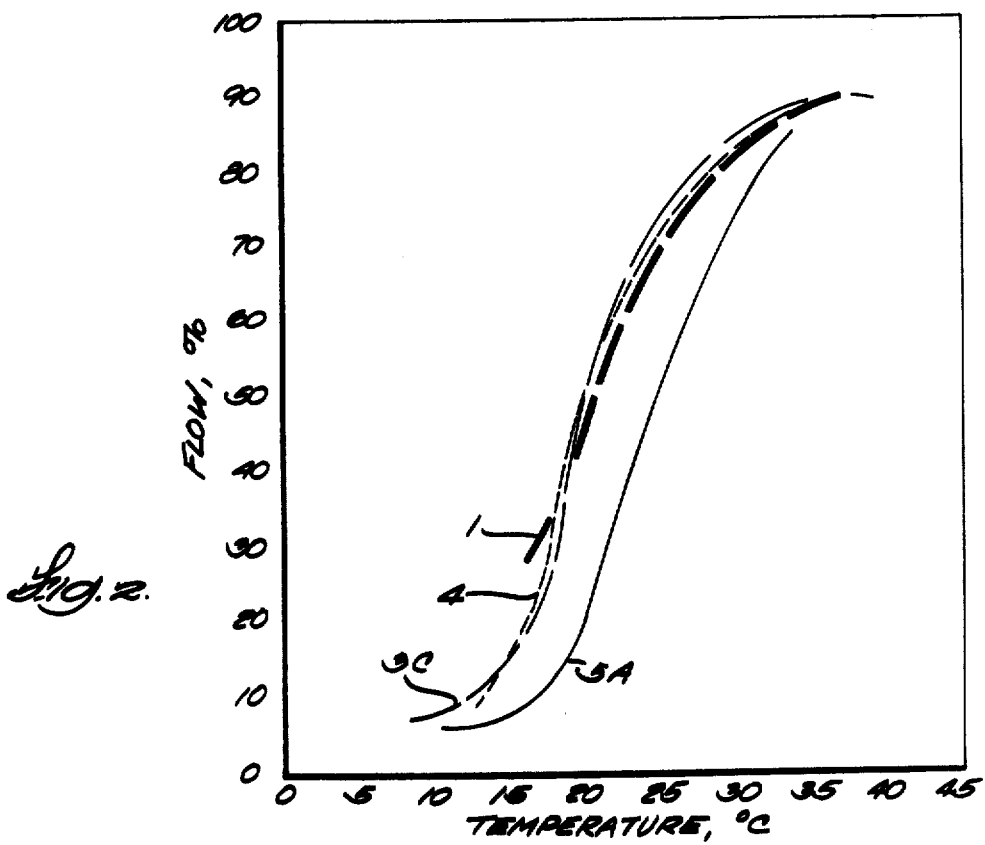
FIG. 2 is a group of curves similar to FIG. 1 showing percent flow versus temperature for the other proportions of the chemical.

In order to evaluate the flow properties of dental impression compounds, equipment was designed and constructed to cast impression compound columns 10 millimeters in diameter and 6 millimeters high and to expose each column to a pressure of 2000 grams at a selected temperature for 10 minutes. The column height was measured before and after exposure to the pressure. The percent decrease in column height is designated as the plastic flow of the material at the selected temperature. The FIGS. 1 and 2 show percent flow versus temperature for various proportions of the components of the composition of the invention.

Various thermo-plastics were tested and hydrogenated wood rosin appeared to have the most favorable and desirable characteristics for a dental impression compound. The particular hydrogenated wood rosin successfully tested is marketed under the trademark "STAYBELITE" a product of Hercules Incorporated. STAYBELITE is highly resistant to oxidation and discoloration and to changes in solubility characteristics exposed to air and sunlight. STAYBELITE has low taste, odor and good thermo-stability.

Various plasticizers were tested and white petrolatum gave good results. Petrolatum has moderate uniformity provided by high compliance with USP specifications, low odor or taste, good heat and light stability and most importantly, good compatibility with hydrogenated wood rosin that results in no tendency to migrate or sweat to the surface of the mixture when cooled to solidification. Mineral oil, which had been tried in earlier experimentation as a plasticizer, had a tendency to migrate to the surface of cooled mixtures when used with STAYBELITE, causing tackiness.

In addition to the thermo-plastic hydrogenated wood rosin and the plasticizer petrolatum, a filler is necessary to maintain the mixture of thermo-plastic and plasticizer when it solidifies in a rigid solid state and to increase the working temperature range of plastic flow between a rigid solid and low viscosity liquid. The filler also is desirable to decrease the surface tackiness of the mixture. Talc and aluminum powders were found suitable as fillers. Commercial grades of Alcan MD 3100 and US Bronze 560 provided good results. Both of these aluminum powders are non-leafing, fine mesh, stearic acid-coated powder with roughly spherical shapes. The Alcan MD 3100 is specified to have 97.0% minimum pass through 325 mesh. The aluminum powder improves thermoconductivity so that when the composition is heated preliminary to brushing on a tray, the impression material will be quickly and uniformly softened to the plastic state so that no local overheating with consequent degradation of the material will occur. Thus, when the compound on the tray is placed in the mounth, all of the mass will be subject to plastic flow. Furthermore, when the completed impression is cooled by cool water, all of the material will rapidly set to the solid state and not be subject to further stress and deformation. When the dental stone is cast in the impression, the heat generated during the thermal stage of the setting stone will be conducted away from the surface of the composition and stone so that the adverse effects of local compound melting and the interpenetration of the plastic and stone with consequent adhesion, and surface damage, will be minimized. Inasmuch as aluminum has a low density, the larger volume per unit weight in the composition means that a given weight percent of aluminum will have a greater effect on the thermal-conductivity of the mixture than a similar amount of other heavier metals. Also the aluminum has less tendency to settle out of the mixture when it is heated to the fluid state as will occur with heavier metals.

In initial tests, aluminum particles in the form of flakes were used in formulating a dental impression compound, but ultimately the choice of spherical or more regularly shaped particles was made because the formulations with aluminum flakes did not have sufficient flow under stress at mouth temperatures. This disadvantage is believed to have been due to an interlocking or interference of relative movement of the aluminum due to the irregular shape of the flakes. In addition, large particles of aluminum can also interfere with obtaining an impression with the necessary fine detail and definition.

The USP talc used in the composition is a native, hydrous magnesium silicate that is moderately uniform in property if it complys with the USP specifications. Its specific gravity of 2.7 to 2.8 is similar to the specific gravity of aluminum of 2.708 so they don't tend to separate in the mixture when in a fluid state.

The following tables 1 and 2 disclose various proportions of STAYBELITE, petrolatum, aluminum and talc and the temperature flow characteristics obtained in flow measurements for these particular compositions. Table 1 contains the data for FIG. 1, which shows percent flow at various temperatures for compositions 115, 116, 117, 118 and 119. FIG. 1 also includes a curve I which shows the desired flow characteristic for this type of dental impression compound. The curve I passes through the recommended maximum permitted flows of 10 percent at 10° C, 20 percent at 15° C, 55 percent at 20° C and through the recommended minimum flow of 85% at 37° C or mouth temperature.

TABLE 1

Sample Formulas and Flows
Weight Percent

| Formula | Staybelite | Petrolatum (White, USP) | Aluminum (US Bronze 560) | Talc (USP) |
|---|---|---|---|---|
| 115 | 78.78 | 5.84 | 5.12 | 10.25 |
| 116 | 77.08 | 7.89 | 5.23 | 9.80 |
| 117 | 77.02 | 8.02 | 4.99 | 9.97 |
| 118 | 86.20 | 8.91 | 4.78 | 0.00 |
| 119 | 76.49 | 8.51 | 5.00 | 10.00 |

| Formula | Temperatures, °C Flow, % | | | | | Mouth Temperature (37° C) |
|---|---|---|---|---|---|---|
| 115 | 15.8 | 21.8 | 27.9 | 34.2 | 39.4 | |
|  | 7.8 | 37.9 | 70.9 | 84.3 | 89.0 | 87.5 |
| 116 | 17.1 | 22.2 | 27.6 | 33.6 | 38.2 | |
|  | 38.1 | 66.7 | 78.8 | 86.2 | 90.5 | 89.4 |
| 117 | 16.2 | 24.8 |  | 31.7 | 37.8 | |
|  | 15.4 | 66.6 |  | 81.4 | 88.2 | 87.8 |

TABLE 1-continued

| | Sample Formulas and Flows | | | | |
|---|---|---|---|---|---|
| 118 |  | 17.7 | 25.1 | 31.4 | 37.0 | |
|  |  | 57.6 | 78.6 | 86.6 | 91.0 | 90.8 |
| 119 | 10.0 | 16.6 | 25.6 |  | 33.7 | 37.1 |
|  | 11.8 | 45.4 | 74.6 |  | 87.5 | 90.3 | 90.3 |

TABLE 2

Trial Batch Formulas and Flows
Weight Percent

| Batch | Staybelite | Petrolatum (White, USP) | Aluminum (Alcan MD 3100) | Talc (USP) |
|---|---|---|---|---|
| 1 | 77.00 | 8.00 | 5.00 | 10.00 |
| 2 | 77.00 | 8.00 | 5.00 | 10.00 |
| 3C | 78.26 | 6.50 | 5.08 | 10.16 |
| 4 | 78.50 | 6.50 | 5.00 | 10.00 |
| 5A | 78.50 | 6.50 | 5.00 | 10.00 |
| 5C | 78.34 | 6.70 | 4.99 | 9.98 |

| Batch | Temperatures, °C Flow, | | | | | | Mouth Temperature % (37° C) |
|---|---|---|---|---|---|---|---|
| 1 |  | 16.2 |  | 26.1 |  | 35.1 | 36.1 | |
|  |  | 28.6 |  | 73.0 |  | 85.5 | 89.0 | 87.6 |
| 2 |  |  |  |  |  |  | 36.2 | |
|  |  |  |  |  |  |  | 89.5 | |
| 3C | 8.6 | 16.0 | 19.5 | 26.4 | 30.9 |  | 38.8 | |
|  | 7.45 | 16.17 | 47.04 | 77.44 | 84.92 |  | 88.52 | 88.2 |
| 4 | 12.4 | 18.4 | 22.6 | 29.1 | 32.9 | 35.4 | 40.0 | |
|  | 8.69 | 40.84 | 61.93 | 79.97 | 85.82 | 89.00 | 89.75 | 89.3 |
| 5A | 10.5 | 16.4 | 22.1 | 29.2 | 35.7 | 36.4 | 37.8 | |
|  | 6.02 | 8.66 | 35.56 | 69.47 | 82.04 | 88.56 | 89.72 | 89.0 |
| 5C |  | 13.9 |  |  |  |  | 36.7 | |
|  |  | 5.83 |  |  |  |  | 86.51 | |

In the experiments recorded in Table 2, the changing from one brand of white USP petrolatum to another can greatly effect the amount of petrolatum needed for desired flow properties. Table 2, Batch 1, had one type of petrolatum (white USP) and Batch 2 had a different type of petrolatum, although in the same proportions as Batch 1. Different percent flow characteristics were achieved between Batches 1 and 2.

The following Table 3 indicates composition ranges for the dental impression compound based on formulas 115 through 119 in Table 1 and Batch 1 of Table 2.

TABLE 3

| | Approximate Compositon Ranges of the Dental Impression Compound, weight percents | | |
|---|---|---|---|
| Range | Wide | Narrow | Optimum |
| Total Filler | 5–25 | 10–20 | 15 |
| Aluminum powder | 5–25 | 5–20 | 5–15 |
| Talc, USP | 0–20 | 0–15 | 0–10 |
| Plasticizer | | | |
| White Petrolatum, USP | 6.5–9.5 | 7.5–8.5 | 7.75–8.25 |
| Plastic | | | |
| Hydrogenated wood rosin | 65.5–88.5 | 71.5–82.5 | 76.75–77.25 |
| Overall Total | 100 | 100 | 100 |

Because the properties of the impression compound depend on selection of the mutually interdependent weight percents of its components, some of the factors that affect the choice should be discussed. Experiment indicates that the total filler content may be varied from about 5 to 25% while maintaining a reasonable plastic flow temperature range centered on mouth temperatures by compensating selection of the plasticizer content. Below about 5% filler content the plastic flow temperature range is more narrow than desired, the surface of the warmed mixture increases in tackiness, and even if the filler is all aluminum powder the thermal conductivity of the mixture will not be much better than that of the plastic alone. Above 25% filler content, the plastic flow temperature range is wider than desired so that it may extend close to room temperatures and result in impressions that will lose detail and accuracy before and during casting of the dental stone positives. For convenience the total filler content of the formulation is initially selected at or near 15%. Of this at least 5% is selected to be aluminum powder so that significant thermal conductivity improvement will be achieved. Additional thermal conductivity improvement is realized with increased aluminum powder content up to the total filler limit. However, the presence of talc as the balance of the total filler content has the advantages of decreasing the mixture's cost and easing the possible selection of another mixture color.

If a pigment were to be used to produce another mixture color, its weight percent would be subtracted from that of the talc so the total filler content would remain constant. The plasticizer content is then selected to provide sufficient flow at mouth temperature.

Because even the ingredients of this compound which have been selected partially for their uniformity do vary slightly in their properties from purchased batch to batch, the correct amount of plasticizer must be selected for a selected total filler content on the basis of flow tests of trial formulations of the components. In practice, the correct amount of plasticizer for 15% filler content has been about 8% with one petrolatum and 6.5% with another. After selecting the filler content and finding the correct plasticizer content through experiment, the plastic content (hydrogenated rosin) is of course, fixed because it is the remainder of the formulation. To insure that each batch of the impression compound has the correct flow characteristics, proper quality control will require that the flow be determined with the proper instruments and methods at a minimum of two temperatures — one between 10° and 15° C, and one at about 37° C. This quality control is especially important whenever new quantities of the components are obtained.

To achieve good results with almost any dental material, requires correct manipulative techniques. This fact is also true in the case of this dental impression material. To obtain good impressions of soft mouth tissues with this material, the correct techniques are required.

We claim:

1. A dental impression composition consisting essentially of a mixture by weight of hydrogenated wood rosin 65.5 to 91.0 percent; white petrolatum 4.0 to 9.5 percent; talc 0 to 20 percent; aluminum powder 5 to 25 percent; total talc and aluminum 5 to 25 percent.

2. A dental impression composition consisting essentially of a mixture by weight of hydrogenated wood rosin 71.5 to 89.0 percent; white petrolatum 6.0 to 8.5 percent; talc 0 to 15 percent; aluminum powder 5 to 20 percent; total talc and aluminum 5 to 20 percent.

3. A dental impression composition consisting essentially of a mixture by weight of hydrogenated wood rosin 76.75 to 88.75 percent; white petrolatum 6.25 to 8.25 percent; talc 0 to 10 percent; aluminum powder 5 to 15 percent; total talc and aluminum 5 to 15 percent.

4. A dental impression composition consisting essentially of a mixture of hydrogenated wood rosin, white petrolatum, aluminum powder and talc in such porportions to have a maximum permitted flow of 10% at 10° C, 20% at 15° C, 55% at 20° C and a minimum flow of 85% at 37° C.

* * * * *